United States Patent [19]
Kaneko et al.

[11] Patent Number: 4,688,175
[45] Date of Patent: Aug. 18, 1987

[54] IMAGE PROCESSOR WITH AUTOMATIC SETTING OF WINDOW WIDTH AND LEVEL FOR INDIVIDUAL BLOCKS OF THE IMAGE

[75] Inventors: Makoto Kaneko; Ichiro Ogura, both of Ootawara; Hiroshi Asahina, Tochigi; Hiroshi Yasuhara, Ootawara, all of Japan

[73] Assignee: Kabushiki Kaisha Toshiba, Kawasaki, Japan

[21] Appl. No.: 655,740

[22] Filed: Sep. 28, 1984

[30] Foreign Application Priority Data

Sep. 30, 1983 [JP] Japan ................................. 58-182683

[51] Int. Cl.$^4$ ..................... G06F 15/68; G01N 23/04; H05G 1/64; H04N 5/32
[52] U.S. Cl. .................................. 364/414; 358/111; 378/99
[58] Field of Search ........................ 364/414; 358/111; 378/99

[56] References Cited

U.S. PATENT DOCUMENTS

| | | | |
|---|---|---|---|
| 4,079,417 | 3/1978 | Scudder, III ....................... | 358/111 |
| 4,105,922 | 8/1978 | Lambert et al. ................ | 358/111 X |
| 4,125,858 | 11/1978 | Hounsfield et al. ............ | 358/111 X |
| 4,438,495 | 3/1984 | Collins et al. ................... | 358/111 X |
| 4,581,635 | 4/1986 | Franke ............................... | 358/111 |
| 4,593,314 | 6/1986 | Siler .................................. | 364/414 X |
| 4,595,949 | 6/1986 | Fenster et al. ....................... | 358/111 |
| 4,642,621 | 2/1987 | Nemoto et al. .................. | 364/417 X |

FOREIGN PATENT DOCUMENTS

| | | | |
|---|---|---|---|
| 0158687 | 9/1984 | Japan ................................... | 358/111 |
| 2061660 | 5/1981 | United Kingdom ................ | 358/111 |

OTHER PUBLICATIONS

Frost, M. M. et al., "A Digital Video Acquisition System for Extraction of Subvisual Information in Diagnostic Medical Imaging", SPIE, vol. 127, Optical Instrumentation in Medicine VI, Sep. 1977, 208-215.

Primary Examiner—Jerry Smith
Assistant Examiner—Clark A. Jablon
Attorney, Agent, or Firm—Finnegan, Henderson, Farabow, Garrett & Dunner

[57] ABSTRACT

An image processing apparatus includes frame memories for storing information of an image to be displayed; a block memory for dividing the information stored in the frame memories into a given number of information blocks and storing the divided information blocks; a microcomputer circuit for automatically determining a desired value of each of LEVEL and WIDTH according to given contents of the divided information blocks; and an image emphasis circuit for window-processing information of the image to be displayed according to the determined value of each of the LEVEL and WIDTH.

13 Claims, 18 Drawing Figures

| CONTENTS (D21A) | ADDRESS (A21A) |
|---|---|
| 0 | 0000 |
| 0 | 0001 |
| 0 | 0002 |
| ⋮ | ⋮ |
| 0 | 0063 |
| ΔW | 0064 |
| 2ΔW | 0065 |
| 3ΔW | 0066 |
| ⋮ | ⋮ |
| (N−1)ΔW | 0317 |
| NΔW | 0318 |
| 255 | 0319 |
| ⋮ | ⋮ |
| 255 | 1021 |
| 255 | 1022 |
| 255 | 1023 |

LEVEL / WIDTH

FIG. 10

IMAGE PROCESSOR WITH AUTOMATIC SETTING OF WINDOW WIDTH AND LEVEL FOR INDIVIDUAL BLOCKS OF THE IMAGE

BACKGROUND OF THE INVENTION

The present invention relates to an image processing apparatus with an automatic window processing function which is well fitted to adapt to X-ray digital fluorography, said window processing serving to improve the quality of an image displayed at a monitor by changing the contrast of the image.

Figure 1:
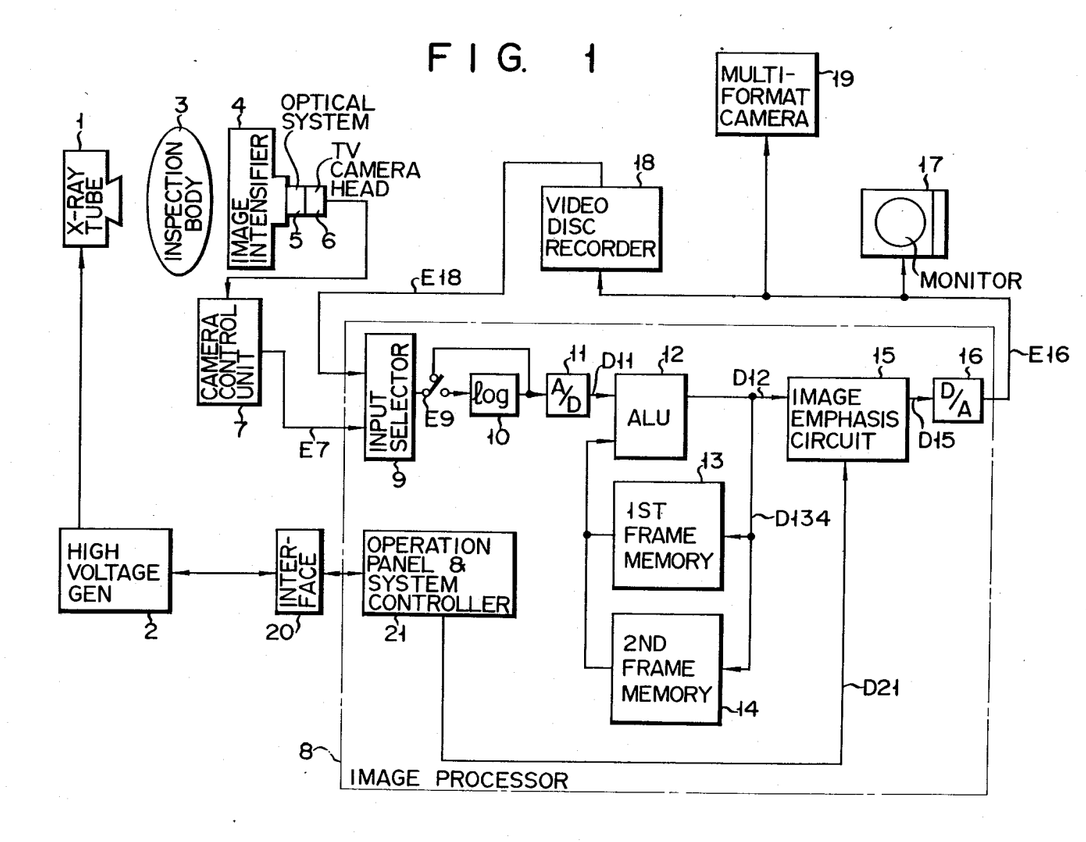
FIG. 1 shows a schematic block diagram illustrating the configuration of an example of an X-ray diagnosis apparatus which is utilized in X-ray digital fluorography.

A typical application of an image processing apparatus with a window processing function is, e.g., an X-ray diagnostic apparatus used in X-ray digital fluorography. Such an apparatus may have a configuration as shown in FIG. 1. In this figure, numeral 1 denotes an X-ray tube. Tube 1 radiates an X-ray to an inspection body 3 upon receiving a high voltage from a high voltage generation apparatus 2. Numeral 4 denotes an image intensifier. Intensifier 4 responds to an X-ray passing through inspection body 3 and converts an image of the passing X-ray into an optical image. The optical image from intensifier 4 is projected onto an image pickup tube via an optical system 5 which contains an iris stop. The image pickup tube is installed in a TV (television) camera head 6. The projected image is obtained as an image signal E7 through a conventional camera control unit 7.

Image signal E7 is supplied to an image processor 8. Processor 8 includes an input selector 9 which receives image signal E7. Selector 9 selects the signal E7 as a selected signal E9. Selected signal E9 is supplied via a switch either directly to an A/D converter 11, or, via a logarithmic function converter (so called "log amplifier") 10 to A/D converter 11 according to the selection of the switch. Signal E9 is converted by A/D converter 11 into a digital image signal D11. Signal D11 is arithmetically processed in a prescribed manner in an arithmetic and logic unit (ALU) 12. An arithmetically processed signal D134 obtained from ALU 12 is stored in a first frame memory 13. The stored contents in first frame memory 13 represents an X-ray image of inspection body 3 to which no X-ray contrast medium is injected. Similarly, another arithmetically processed signal D134 from ALU 12 is stored in a second frame memory 14. Second frame memory 14 may have the same configuration as first frame memory 13. The stored contents in second frame memory 14 represents an X-ray image of inspection body 3 to which an X-ray contrast medium is injected.

One of the above two arithmetically processed signals (D134) stored in frame memories 13 and 14 is subtracted in ALU 12 from the other, so that a subtracted image signal D12 is generated. Subtracted image signal D12 is supplied to an image emphasis circuit (window circuit) 15. In circuit 15, the contrast of an image of signal D12 to be displayed is changed or emphasized. A contrast-emphasized image signal D15 corresponding to signal D12 is obtained from image emphasis circuit 15. Signal D15 (digital in form) is converted to an analog image signal E16 via a D/A converter 16. Signal E16 is supplied to a monitor 17 located at the outside of processor 8. In monitor 17, an image of signal E16 is displayed. At the same time, signal E16 is supplied to a video disc recorder 18, and the image information of signal E16 is recorded on a video disc. Further, signal E16 is transferred to a multiformat camera 19 in which the transferred signal is photographed on a film. A reproduced image signal E18 from recorder 18 is supplied to input selector 9. When selector 9 selects signal E18 in place of signal E7, processor 8 performs the above-mentioned signal processing for signal E18.

In FIG. 1, numeral 20 denotes an X-ray interface for interfacing the high voltage generation apparatus 2 with the image processor 8. Numeral 21 denotes an operation panel (for processor 8, etc.) & system controller which controls apparatus 2 via interface 20 or which manipulates the respective elements of processor 8.

Incidentally, the configuration of FIG. 1 may be modified or replaced by one as disclosed in U.S. Pat. No. 4,204,225 (Mistretta) issued on May 20, 1980 or U.S. Pat. No. 4,204,226 (Mistretta et al.) issued on May 20, 1980. All disclosures of these U.S. patents are incorporated in the present application.

Figure 2:
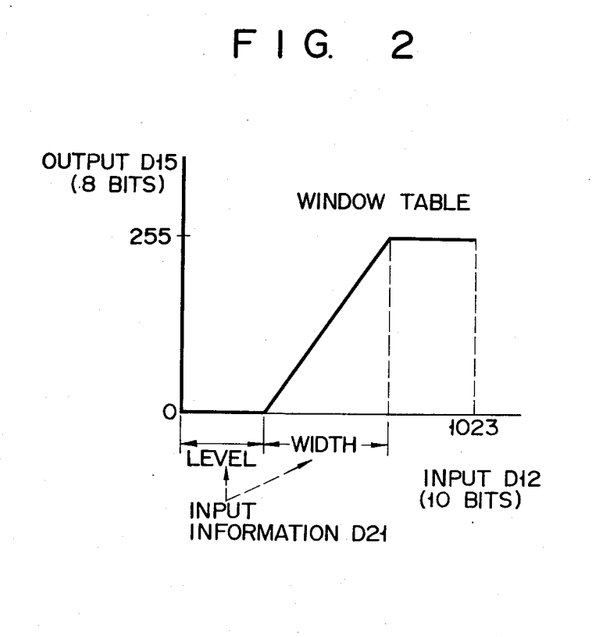
FIG. 2 shows an input-output relationship (window table) of the window processing according to the configuration of FIG. 1.

According to an X-ray apparatus as mentioned above, information D21 of a gradation range (hereinafter referred to as "WIDTH") and gradation level (hereinafter referred to as "LEVEL") for window processing is supplied from operation panel/system controller 21 to image emphasis circuit 15. Then, window processing is performed in circuit 15 so as to improve the quality of a displayed image, by changing the contrast of the image according to the values of LEVEL and WIDTH. An example of a window table indicating the relation among input D12, output D15, LEVEL and WIDTH in the window processing is shown in FIG. 2. In FIG. 2, window input D12 is represented by 10 bits data (0 to 1023 in decimals) and window output D15 is represented by 8 bits data (0 to 255 in decimals). In order to obtain 8-bit image data (D15) without substantially reducing the quantity of 10-bit input information (D12), the window table as shown in FIG. 2 is provided.

Using an apparatus as shown in FIG. 1, it is difficult to quickly determine an optimum value of each of LEVEL and WIDTH by viewing the image displayed at monitor 17. In other words, it is not easy to optionally determine, by viewing the monitor, the desired values of LEVEL and WIDTH by experimentally changing the values of LEVEL and WIDTH. Thus, in using the above-mentioned apparatus, in which the values of LEVEL and WIDTH are individually determined by various operators, much skill and time is required for the window processing. In addition, the contrast of an image obtained according to the above described window processing is not always optimal.

SUMMARY OF THE INVENTION

It is accordingly an object of the present invention to provide an image processing apparatus with an automatic window processing function which can automatically determine the optimal values of LEVEL and WIDTH.

Another object of the present invention is to provide an X-ray diagnosis apparatus being well fitted to adapt to X-ray digital fluorography, in which a special window processing is performed so that a desired value of each of LEVEL and WIDTH is automatically determined, thereby readily obtaining an image with optimum contrast.

To achieve the above objects, an image processing apparatus of the invention comprises frame memory means (13 and/or 14) for storing information of an image to be displayed; block memory means (22) for dividing the information stored in the frame memory means into a given number of information blocks and storing the divided information blocks; determination means (21A) for automatically determining a desired value of each of LEVEL and WIDTH according to given contents of the divided information blocks; and window processing means (15) for processing information of the image to be displayed according to the determined value of the LEVEL and WIDTH.

According to the present invention, it is possible to obtain an image processing apparatus or X-ray diagnosis apparatus having an "AUTO WINDOW" function which automatically provides proper window data for an image displayed on the monitor of which improves the quality of the image by automatically changing the contrast thereof.

DETAILED DESCRIPTION OF THE PREFERRED EMBODIMENT

Figure 3:
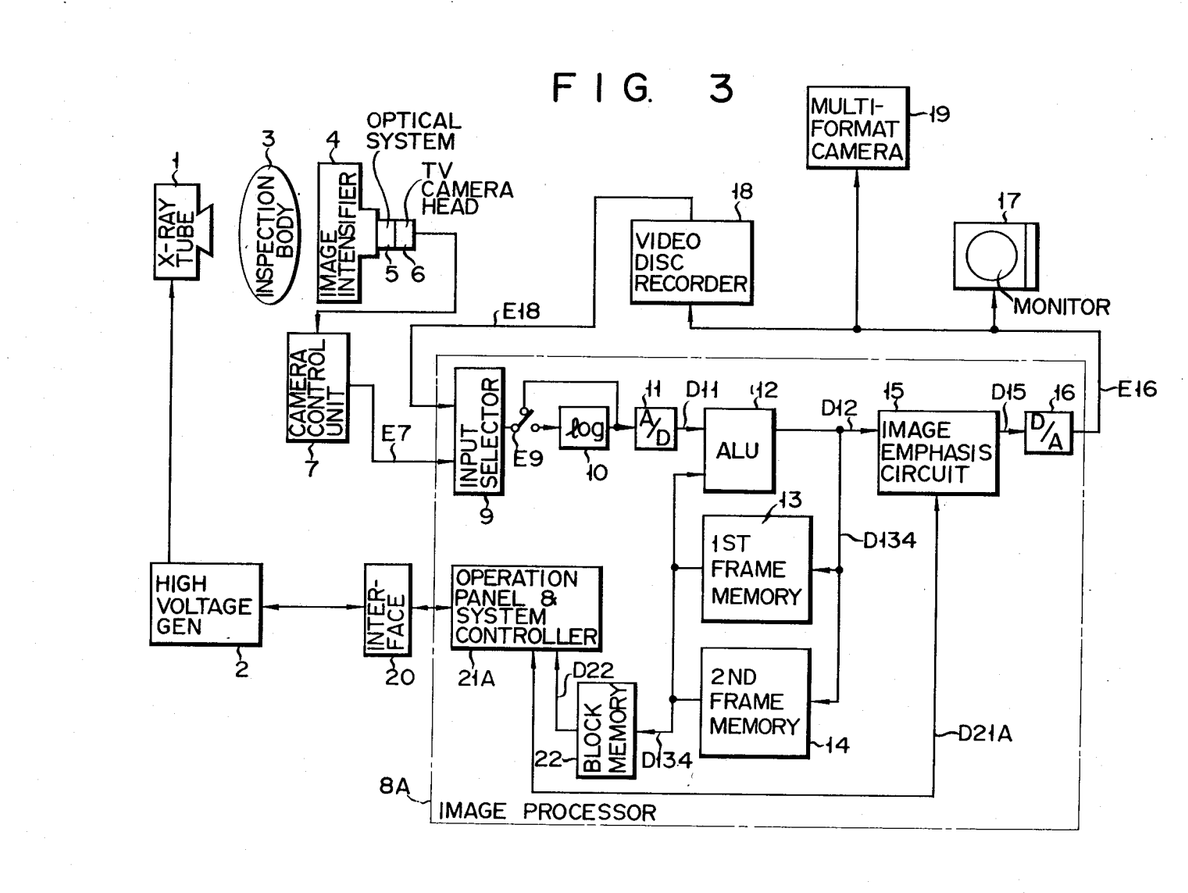
FIG. 3 shows a schematic block diagram illustrating one configuration of an embodiment of the present invention.

FIG. 3 shows an embodiment of the present invention, wherein a schematic configuration of an X-ray diagnosis apparatus utilized in X-ray digital fluorography is illustrated. The configuration of the X-ray diagnosis apparatus in FIG. 3 is substantially the same as that in FIG. 1, except that a block memory 22 is specially provided in an image processor 8A. In the following, detailed description regarding the common configurations between FIGS. 1 and 3 are omitted to avoid redundant explanation. Only the characteristic portion in FIG. 3 will be described in detail hereinafter.

Figure 4:
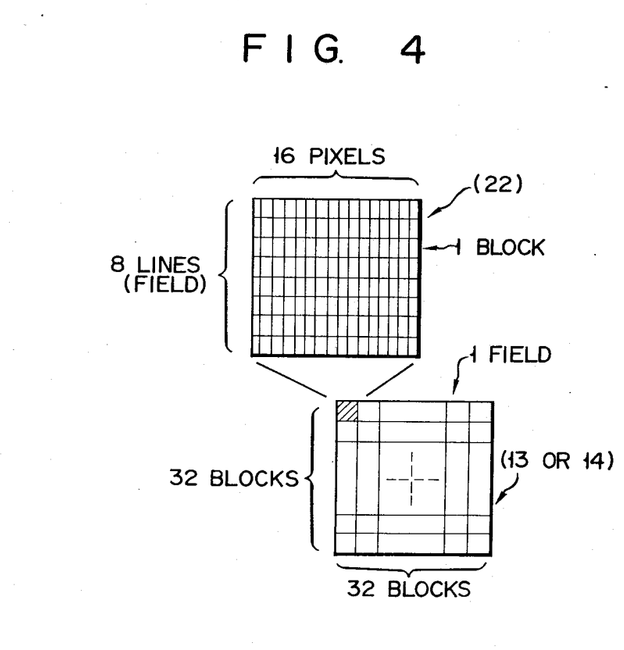
FIG. 4 shows a schematic diagram illustrating the relation between the contents of the frame memory and block memory in FIG. 3.

In FIG. 3, block memory 22 is located at the output side of first frame memory 13 and second frame memory 14 in processor 8A. As shown in FIG. 4, information or image signals for one frame stored in first frame memory 13 and/or second frame memory 14 is divided into 32×32 information blocks each having a predetermined size of 8×16 pixels, for example. An average of gradations for respective information blocks of the first and/or second frame memories are stored in block memory 22.

Figure 5:
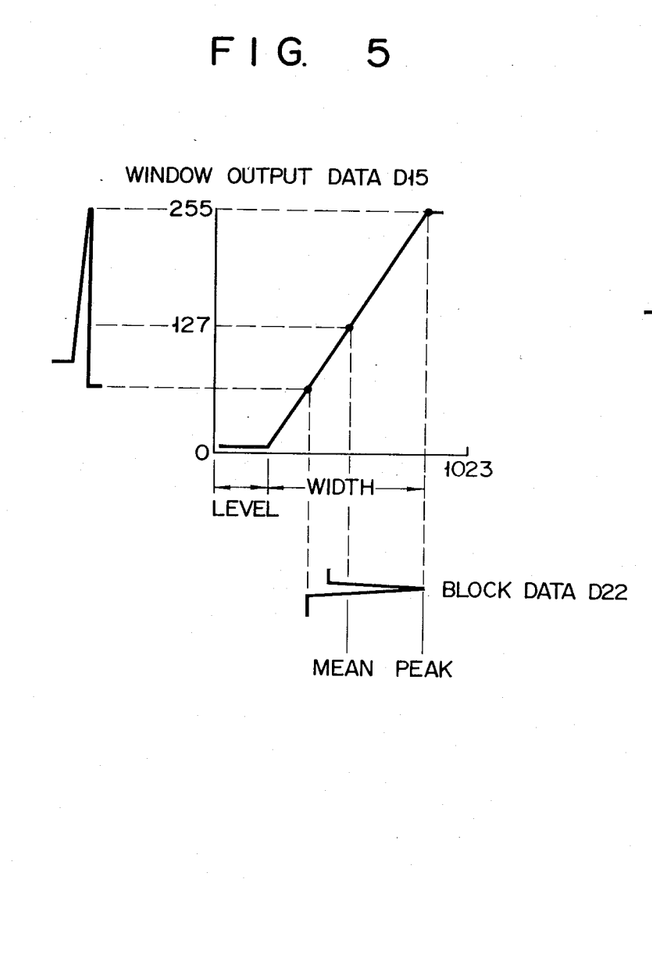
FIG. 5 illustrates the relationship between the window processing (peak value method) and the information (block data) from a block memory in the FIG. 3 embodiment.
Figure 6:
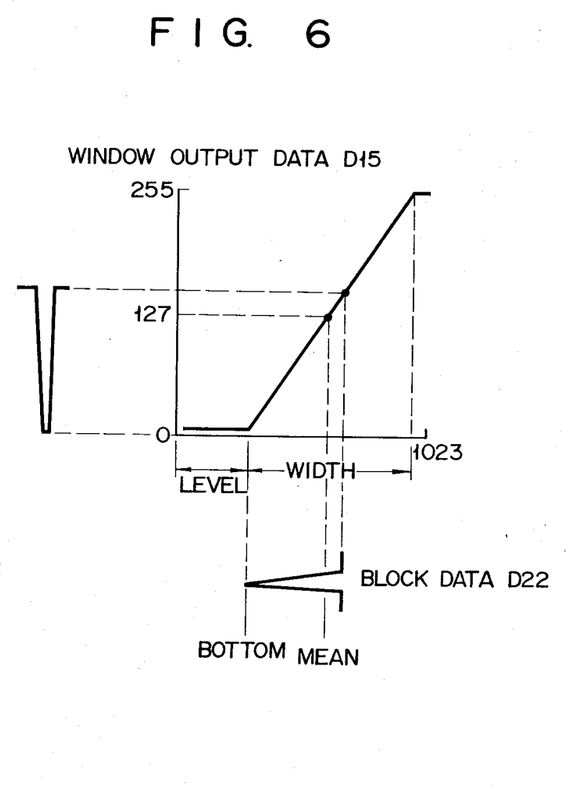
FIG. 6 illustrates the relationship between the window processing (bottom value method) and the information (block data) from a block memory in the FIG. 3 embodiment.

An operation panel/system controller 21A, which serves to control processor 8A as well as the whole system, accesses block memory 22 to read out the contents thereof. In controller 21A, the average value (or the center value) and the peak value (or the bottom value) of the contents in block memory 22 are obtained. The average or center value is used as a mean value of a window output D15, as shown in FIGS. 5 and 6. The obtained peak value is used as the maximum value of window output D15 (FIG. 5). Or, the obtained bottom value is used as the minimum value of window output D15 (FIG. 6). The value of LEVEL may be obtained from the bottom value:

$$\text{LEVEL} = \text{the bottom value} \tag{1}$$

The value of WIDTH may be obtained in controller 21A according to the following calculation:

$$\text{WIDTH} = |\text{the center value} - \text{the bottom value}| \times 2 \tag{2}$$

or $$\text{WIDTH} = |\text{the peak value} - \text{the center value}| \times 2 \tag{3}$$

or $$\text{WIDTH} = |\text{the peak value} - \text{the bottom value}| \tag{4}$$

Operation panel/system controller 21A supplies data D21A of the window curve (FIG. 5 or 6) to image emphasis circuit 15 so that an automatic window processing (AUTO WINDOW) is effected.

Figure 7:
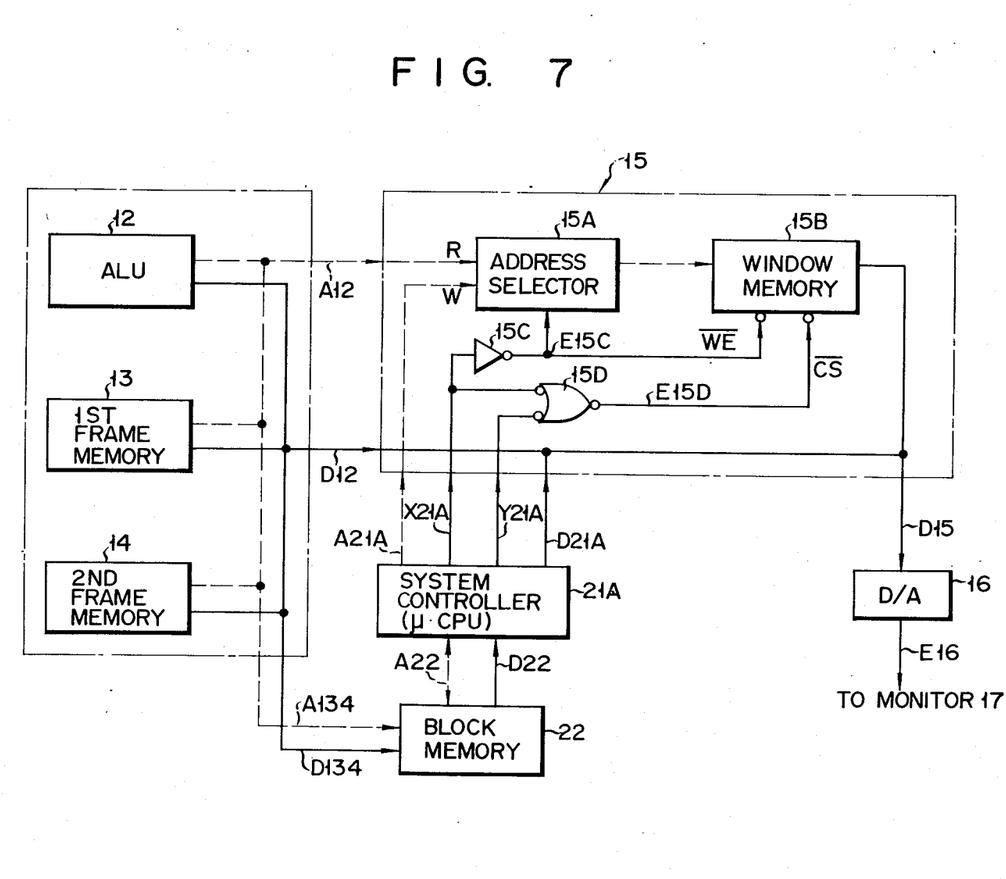
FIG. 7 shows details of the image emphasis circuit (window circuit) in the FIG. 3 embodiment.

FIG. 7 shows details of image emphasis circuit (window circuit) 15 and its associated circuits.

In FIG. 7, arithmetically processed signal D134 from first frame memory 13 and/or second frame memory 14 is supplied to block memory 22 (details thereof will be described later with reference to FIG. 10). Address data A12 for subtracted image signal D12 from ALU 12 is supplied to an input R of an address selector 15A. An input W of selector 15A receives address data A21A from a microcomputer provided in system controller 21A. Whether A12 or A21A is selected is determined by the logic level of a write enable signal E15C. Signal E15C is obtained through an inverter 15C by inverting a write command X21A supplied from system controller 21A. The selected address data A12 or A21A from selector 15A is supplied to the address input of a window memory (static RAM) 15B. Memory 15B receives write enable signal E15C and a chip select signal E15D. Signal E15D corresponds to the logic AND of write command X21A and a select command Y21A. Select command Y21A is obtained from system controller 21A. The logical AND operation of X21A and Y21A is performed by a two inverted inputs type NOR gate 15D (which is functionally equivalent to an AND gate). Data D21A to be stored in memory 15B is obtained from system controller 21A.

When write command X21A is logic "1," write enable signal E15C is logic "0" so that selector 15A selects address data A21A from system controller 21A and the mode of memory 15B becomes WRITE. In this case, when command Y21A is "0" (command X21A is "1"), chip select signal E15D is logic "0" so that memory 15B is enabled in the WRITE mode. Then, write data D21A, which corresponds to block data D22 from block memory 22, is written in memory 15B at the given location designated by address data A21A. (How the data D21A is obtained will be described latter.)

When write command X21A is logic "0", signal E15C becomes logic "1" so that selector 15A selects address data A12 from ALU 12 and memory 15B is in the READ mode. In this case, when select command Y21A is "1" (write command X21A is "0"), chip select signal E15D is logic "0" so that memory 15B is enabled in the READ mode. Then, the stored contents of memory 15B is read out according to address data A12. The read out data from memory 15B becomes contrast-emphasized image signal D15, and signal D15 is supplied to D/A converter 16.

When both commands X21A and Y21A are logic "1," the logic level of chip select signal EA15D becomes "1" so that window memory 15B is unselected or disenabled. In this case, no window processing (contrast-emphasizing) is performed, and subtracted image signal D12 from ALU 12 is directly transferred to D/A converter 16.

Figure 8:
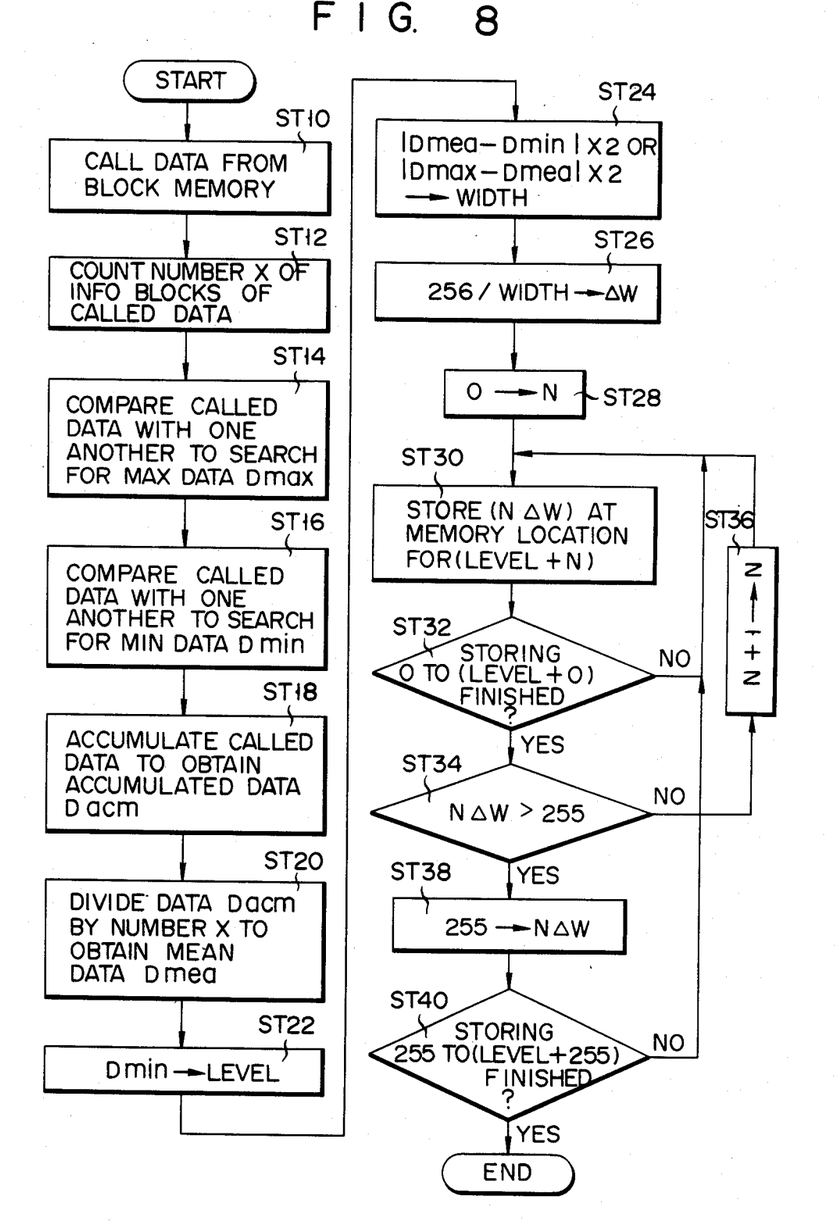
FIG. 8 is a general flow chart explaining the operation of the microcomputer (21A) in FIG. 7.

FIG. 8 is a general flow chart explaining how the data D21A is obtained from the contents (block data D22) of block memory 22. The flow of FIG. 8 is effected under the control of the microcomputer in system controller 21A.

First, a key manipulation of controller 21A triggers the microcomputer to start the program of the flow in FIG. 8. The microcomputer supplies address data A22 to block memory 22 and calls block data D22 from the designated address of data A22 (ST 10). The number X of information blocks of the called data is counted (ST12). For instance, when data D22 of all blocks (32×32 blocks as shown in FIG. 4) are called, number X is 1024. When only a partial data D22 of ROI (region of interest) is called, number X is, e.g., 128. All of the called data D22 are temporarily stored in a RAM (not shown) of the microcomputer. The microcomputer compares all data in the RAM with one another and detects data Dmax having the maximum value (ST 14). Then, the microcomputer compares all data in the RAM with one another and detects data Dmin having the minimum value (ST 16). The microcomputer accumulates all data in the RAM to obtain accumulated (or total) data Dacm (ST18). Next, the microcomputer divides the accumulated data Dacm by the number X of the called data blocks and obtain mean data Dmea (ST 20). Thus, Dmea=Dacm/X.

According to the aforementioned equation (1), minimum data Dmin is entered as the value of LEVEL (ST 22). The microcomputer calculates the value of WIDTH according to the aforementioned equation (2) or (3) (ST 24). When contrast-emphasized image output (window output) D15 is represented by 8 bits data, the unit of gradation for window processing may be represented as:

$$\Delta W = 256/\text{WIDTH} \quad (5)$$

The gradation may be generally represented by N$\Delta$W. Here, N is a given optional number (N=1, 2, 3, - - -). The microcomputer calculates the value of $\Delta$W according to equation (5) and enters the calculated value of $\Delta$W (ST 26). Then, the microcomputer initializes the value N of N$\Delta$W to zero (ST 28).

Figure 9:
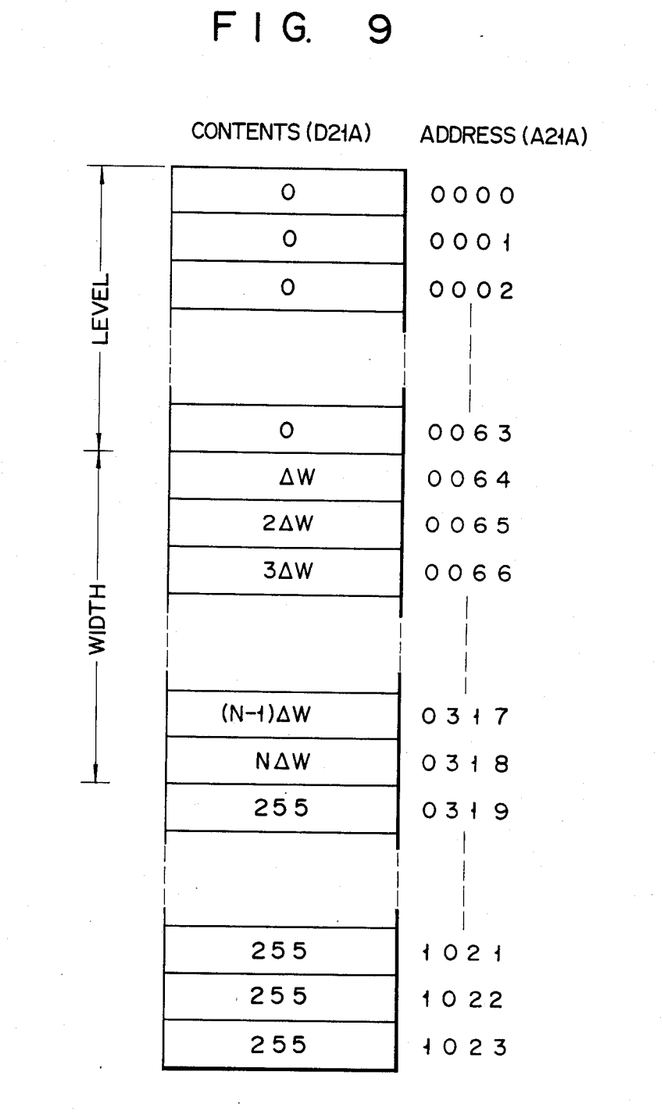
FIG. 9 shows a memory location of the block memory in FIG. 7, the contents of said memory location being determined by the microcomputer operation of FIG. 8.

FIG. 9 shows a memory location of block memory 15B in FIG. 7. The value of gradation N$\Delta$W (in this case, 0×$\Delta$W=0) is stored in an address LEVEL+N=address LEVEL+0 of memory 15B (ST 30). The first one of zero data (=LEVEL) is stored in the address "0000" of memory 15B (FIG. 9). Whether or not all data for LEVEL are stored in memory 15B is checked in step ST 32 according to the number of minimum data Dmin obtained at step ST 16. When data for LEVEL remains (NO at ST 32), the flow returns to step ST 30. When the number of data for LEVEL is 64, for example, addresses "0000" to "0063" of memory 15B are filled with data zero (FIG. 9). When all data (64 of zero data) are stored in addresses "0000" to "0063", storing the zero (LEVEL) data to the addresses of LEVEL+0 is finished (YES at ST 32).

After the completion of storing for addresses LEVEL+0, the value of N$\Delta$W is compared with a specific data (e.g., 255) at step ST 34. Immediately after step ST 32, the value of N$\Delta$W is 0. Accordingly, N$\Delta$W is less than 255 (NO at ST 34). Then, number N is incremented by "1" at step ST36, and the flow is returned to step ST30. In this case, since N=1, N$\Delta$W is equal to $\Delta$W and data $\Delta$W is stored in the address LEVEL+1 or address "0064" (FIG. 9). When the maximum number of N which avoids the establishment of the relation "N$\Delta$W>255" is 255, for example, data $\Delta$W to 255$\Delta$W are stored in addresses "0064" to "0318" (FIG. 9). When N$\Delta$W exceeds "255" at N=256 (YES at ST 34), data "255" in place of N$\Delta$W (>255) is stored in the address "0319" (ST 38). Next, whether or not the storing of data "255" in place of N$\Delta$W (>255) is completed is checked (ST 40). When data for N$\Delta$W (>255) remains (NO at ST 40), the flow returns to step ST 30. When addresses "0320" to "1023" of memory 15B are filled with data 255 in similar manner (FIG. 9), storing the data of "255" to memory 15B is finished (YES at ST 40). Thus, when N$\Delta$W exceeds "255" at and after N=256 (YES at ST 34), "255" data for N$\Delta$W (>255) are equally stored in addresses "0319" to "1023" of memory 15B.

The contents (D21A) of window memory 15B (FIG. 9) are thus obtained from block data D22.

Figure 10:
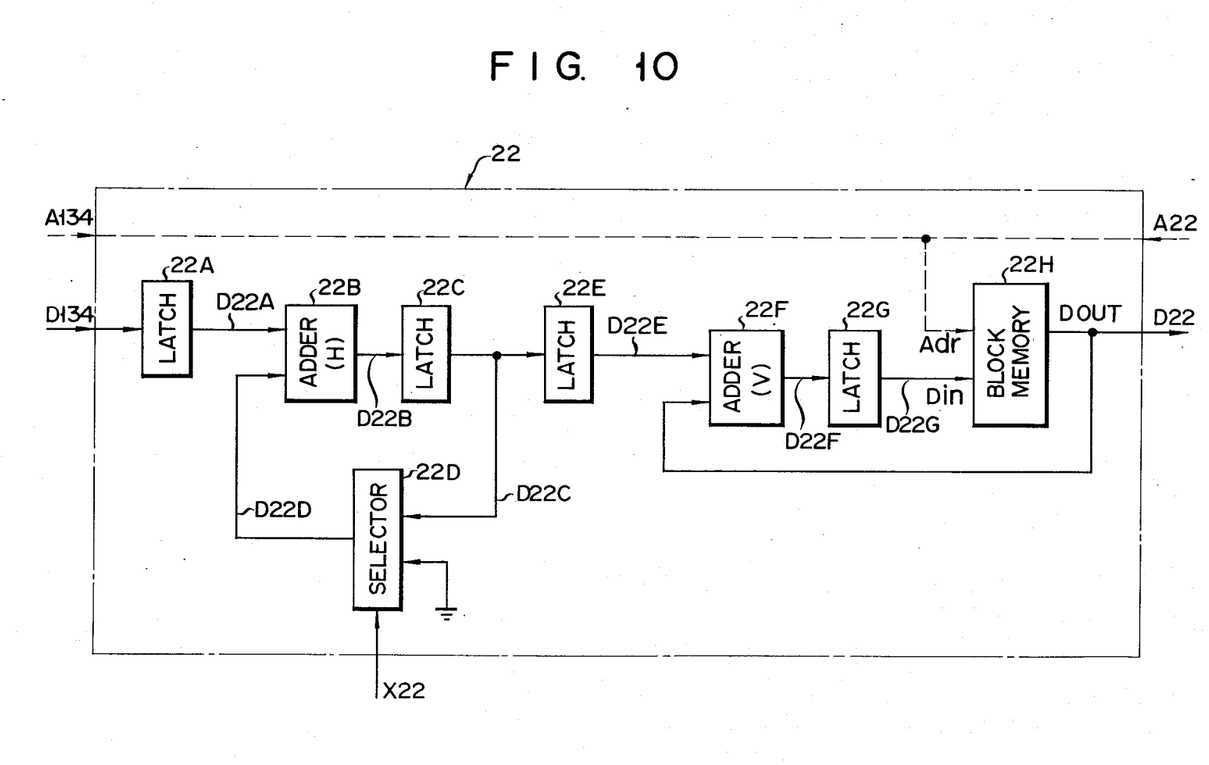
FIG. 10 shows a circuit configuration of the block memory in FIG. 7.
Figures 11A, 11B, 11C, 11D, 11E:
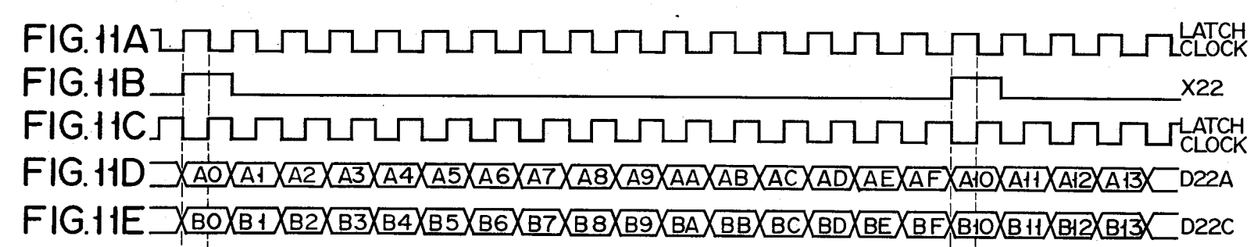
FIGS. 11A to 11H show timing charts explaining the operation of the circuit of FIG. 10.
Figures 11F, 11G:
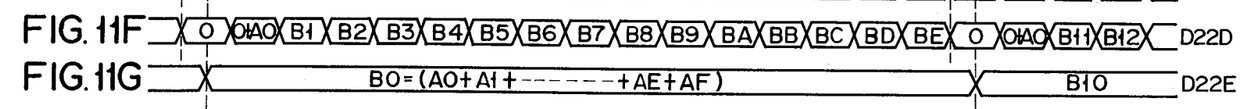
Figure 11H:
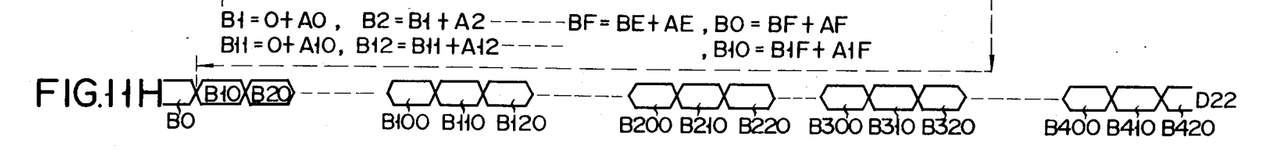

FIG. 10 shows details of block memory 22 in FIG. 7. FIGS. 11A to 11H show timing charts explaining the operation of the circuit of FIG. 10. Arithmetically processed signal D134 from first and/or second frame memories 13 and/or 14 is temporarily stored in a latch 22A. Latched data D22A (FIG. 11D) from latch 22A is supplied to a horizontal adder 22B. Adder 22B receives data D22D (FIG. 11F) from a data selector 22D. At this time, selector 22D selects zero (ground potential) data according to the logic "1" of a selection instruction X22 (FIG. 11B). Then, adder 22B outputs added data D22B corresponding to data D22A. Data D22B is temporarily stored in a latch 22C by a latch clock (FIG. 11A). Latched data D22C (FIG. 11E) from latch 22C is temporarily stored in a latch 22E by a latch clock (FIG. 11C), while it is supplied to selector 22D. At this time, the logic level of instruction X22 is "0" so that selector 22D selects data D22C as the selected data D22D. In this case, the newly latched data D22C (FIG. 11E) corresponds to the sum of data D22A and data D22D (=D22C obtained by the preceding latch).

According to the above operation, horizontal data for 16 pixels (one line data of one block as illustrated in FIG. 4) is accumulated in latch 22E.

Accumulated data D22E (FIG. 11G) from latch 22E is supplied to a vertical adder 22F. Adder 22F receives data D22 from block memory 22H. Then, adder 22F outputs added data D22F corresponding to D22E+D22. Data D22F is temporarily stored in a latch 22G. Latched data D22G from latch 22G is stored in block memory 22H at the memory location being designated by address data A134 which is supplied from frame memories 13 and/or 14 or ALU 12.

According to the above operation, vertical data for 8 lines of one block as illustrated in FIG. 4 is accumulated in block memory 22H. Data D22 (FIG. 11H) for each block is thus stored in block memory 22H.

Address data A22 for reading out the contents D22 of block memory 22 is supplied from the microcomputer in system controller 21A (FIG. 7).

According to one embodiment of the present invention, even if an operator is not skilled in the manipulation of window processing, an image with the optimum contrast can be readily obtained at monitor 17.

In the above embodiment, the average value of divided blocks of the image signal stored in the frame memory is obtained, not the average of respective pixels. This is because the average of pixels is liable to be subjected to noise, an accuracy of the order of a pixel unit is not required in practice, and the control speed for AUTO WINDOW based on the average of pixels becomes low.

The present invention should not be limited to the embodiment as described above and as illustrated in the figure. It may be variously embodied by changing or modifying the above embodiment without departing from the scope of the claimed invention.

For instance, when the window curve has a linear functional characteristic as shown in FIG. 5 or 6, the window curve may be determined from two data, i.e., from the peak value and the bottom value of data in block memory 22 (not utilizing the average value). These two data may be optional. Each of these two optional data may be different data of 1/3, 2/5, 3/7, etc., of the peak value, for example. The information of the determined window curve is supplied to image emphasis circuit 15 so that an automatic window control is performed.

On the other hand, the window curve obtained from information in block memory 22, which is supplied to image emphasis circuit 15 so as to achieve an automatic window control, is not restricted to one having a linear functional characteristic as shown in FIG. 5 or 6, but the window curve may have second or more higher order (2nd., 3rd., and so on) functional characteristic.

Block memory 22 may perform the automatic window control by receiving an image signal from the input side of frame memories 13 and 14, not from the output side thereof. In this case, in an automatic window control, the image signal may be directly written in block memory 22, without passing through frame memories 13 and/or 14, in parallel with the writing for frame memories 13 and/or 14.

Further, data to be written in block memory 22 may be an average of given partial blocks of images in two or more frame memories, not an average of the whole image in first and second frame memories 13 and 14. The key is that the data to be written in block memory 22 should correspond to a specific value, e.g., the average of selected respective blocks of an image to be finally displayed. Data to be written in block memory 22 and to be used for an automatic window control may correspond to a prescribed area in a part of the image, e.g., a region of interest (ROI), not to the whole area of the image.

In addition, the present invention is not limited to an X-ray diagnosis apparatus utilized in X-ray digital fluorography. This invention may be applied to various image processing apparatus such as X-ray digital radiography, ultrasonic testing apparatus, etc., in which image data is processed in digital form.

According to an embodiment of the present invention, it is possible to obtain an X-ray diagnosis apparatus having an "AUTO WINDOW" function or an automatic window processing which improves the quality of the displayed image.

What is claimed is:

1. An image processing apparatus comprising: frame memory means for storing information of an image to be displayed;
   block memory means coupled to said frame memory means, for dividing said information stored in said frame memory means into a given number of information blocks, and for then storing said information blocks;
   calculating means coupled to said block memory means for calculating a value of each of LEVEL and WIDTH data according to the contents of said information blocks; and
   window processing means coupled to said calculation means which is responsive to said information of said image to be displayed, for processing said information of said image to be displayed according to said determined value of each of said LEVEL and WIDTH data, said window processing means providing output data used for an image display.

2. An apparatus of claim 1, wherein said image processing apparatus is adapted for use as a diagnostic apparatus in X-ray digital fluorography.

3. An apparatus of claim 2, wherein said frame memory means includes:
   a first frame memory for storing first information of said image to be displayed, said first information representing an X-ray image of an inspection body to which no X-ray contrast medium is injected;
   a second frame memory for storing second information of said image to be displayed, said second information representing an X-ray image of said inspection body to which an X-ray contrast medium is injected; and
   means responsive to the stored contents of each of said first and second frame memories, for subtracting the stored contents of one of said first and second frame memories from the stored contents of the other thereof, and providing difference data corresponding to the information of said image to be displayed, said difference data being supplied to said window processing means so that said difference data is window-processed to generate said output data.

4. An apparatus of claim 1, wherein each of said divided information blocks is formed of a predetermined number of pixels which are arranged regularly.

5. An apparatus of claim 4, wherein said block memory means includes:

accumulator means for accumulating information of said pixels contained in the information of said image to be displayed; and accumulation memory means for storing said accumulated information of said pixels and providing block data which is used in said determination means for determining the value of each of said LEVEL and WIDTH data.

6. An apparatus of claim 5, wherein said calculation means includes:

first means coupled to said accumulation memory means for detecting minimum data (Dmin) of a selected portion of said block data;

second means coupled to said accumulation memory means for detecting mean data (Dmea) of said selected portion of said block data;

third means coupled to said first means, for generating said LEVEL data from said minimum data (Dmin); and fourth means coupled to said first means and to said second means, for generating said WIDTH data from said minimum data (Dmin) and said mean data (Dmea) according to the following relation:

WIDTH = $Dmea - Dmin \times 2$.

7. An apparatus of claim 5, wherein said calculation means includes:

first means coupled to said accumulation memory means for detecting minimum data (Dmin) of a selected portion of said block data;

second means coupled to said accumulation memory means for detecting mean data (Dmea) of said selected portion of said block data;

third means coupled to said accumulated memory means for detecting maximum data (Dmax) of the selected portion of said block data;

fourth means coupled to said first means, for generating said LEVEL data from said minimum data (Dmin); and fifth means coupled to said third means and to said second means, for generating said WIDTH data from said maximum data (Dmax) and said mean data (Dmea) according to the following relation:

WIDTH = $Dmax - Dmea \times 2$.

8. An apparatus of claim 5, wherein said calculation means includes:

first means coupled to said accumulation memory means for detecting minimum data (Dmin) in a selected portion of said block data;

second means coupled to said accumulation memory means for detecting maximum data (Dmax) of the selected portion of said block data;

third means coupled to said first means, for generating said LEVEL data from said minimum data (Dmin); and fourth means coupled to said first means and to said second means, for generating said WIDTH data from said minimum data (Dmin) and said maximum data (Dmax) according to the following relation:

WIDTH = $Dmax - Dmin$.

9. An apparatus of claim 5, wherein said window processing means includes:

window memory means for storing a window curve data which is defined by said LEVEL and WIDTH data and is used for the window processing, wherein address data for writing said LEVEL and WIDTH data into said window memory means is obtained from said calculating means and address data for reading said LEVEL and WIDTH data from said window memory means is obtained from said frame memory means.

10. An image processing apparatus comprising:

frame memory means for storing data for an image to be displayed;

block memory means, coupled to said frame memory means, for dividing said image data stored in said frame memory means into a predetermined number of segments, and storing the segments of said image data;

image enhancing means, coupled to said block memory means, including window processing means for changing the light intensity of said image data by comparing said image data against a Level as a threshold, and a Width as a range, and selectively increasing or decreasing the light intensity of said image data according to the result of said comparing to improve the contrast of image, and means for determining said Level and Width according to the distribution of the segments of said image data; and means, coupled to said image enhancing means, for supplying an output of said image enhancing means to a display for displaying said image improved in contrast.

11. An apparatus of claim 10, wherein said means for determining said Level and Width values is operative to determine said values of Level and Width corresponding to the distribution of light intensity of a plurality of the segmentized image data.

12. An apparatus of claim 11, wherein said means for determining Level and Width of the window processing is operative to correlate the lowest, mean, and highest values of said segments of image data to said values of Level and Width.

13. An X-ray diagnosis apparatus comprising:

X-ray photograph means for obtaining an analog image signal of an object to be inspected in accordance with an X-ray passing through said object;

A/D converter means for converting said analog image signal into a digital image signal;

frame memory means for storing picture information corresponding to said digital image signal;

block memory means for dividing said picture information stored in said frame memory means into a prescribed number of information blocks, and storing said divided information blocks;

first arithmetic means for obtaining an average value of gradations in the respectively divided information blocks, each of said divided information blocks corresponding at least to a given part of said picture information;

memory means for storing the average value of gradations in said respective divided information blocks obtained in said first arithmetic means;

second arithmetic means for obtaining at least two values of the average value from said memory means, the peak value of gradations in the respective divided information blocks and the bottom value of gradations in the respective divided information blocks, and for obtaining, in accordance with the above at least two of obtained values, window information which designates an image emphasis characteristic of window processing; and image emphasis means for window-processing said picture information based on said window information so that the contrast of said picture information is emphasized, and for providing contrast emphasized information for a display or a record.

* * * * *